(12) United States Patent
Yadav (10) Patent No.: US 7,081,267 B2
(45) Date of Patent: Jul. 25, 2006

(54) NANOSTRUCTURED POWDERS AND RELATED NANOTECHNOLOGY

(75) Inventor: Tapesh Yadav, Tucson, AZ (US)

(73) Assignee: NanoProducts Corporation, Longmont, CO (US)

( * ) Notice: Subject to any disclaimer, the term of this patent is extended or adjusted under 35 U.S.C. 154(b) by 125 days.

(21) Appl. No.: 10/614,845

(22) Filed: Jul. 8, 2003

(65) Prior Publication Data

US 2004/0005485 A1 Jan. 8, 2004

Related U.S. Application Data

(63) Continuation of application No. 09/988,901, filed on Nov. 19, 2001, now Pat. No. 6,610,355, which is a continuation of application No. 09/251,313, filed on Feb. 17, 1999, now Pat. No. 6,387,560, which is a continuation of application No. 08/739,257, filed on Oct. 30, 1996, now Pat. No. 5,905,000, which is a continuation-in-part of application No. 08/730,661, filed on Oct. 11, 1996, now Pat. No. 5,952,040, which is a continuation-in-part of application No. 08/706,819, filed on Sep. 3, 1996, now Pat. No. 5,851,507, and a continuation-in-part of application No. 08/707,341, filed on Sep. 3, 1996, now Pat. No. 5,788,738.

(51) Int. Cl.
*H01M 5/12* (2006.01)
*C23C 16/00* (2006.01)

(52) U.S. Cl. .................. 427/115; 427/124; 427/126.1; 427/248.1; 427/250; 264/12

(58) Field of Classification Search ................ 427/115, 427/124, 126.1, 248.1, 250, 2; 429/30, 40; 264/12
See application file for complete search history.

(56) References Cited

U.S. PATENT DOCUMENTS

| | | | |
|---|---|---|---|
| 4,642,207 A | 2/1987 | Uda et al. | |
| 5,128,081 A | 7/1992 | Siegel et al. | |
| 5,147,448 A | 9/1992 | Roberts et al. | |
| 5,149,381 A | 9/1992 | Grewe et al. | |
| 5,355,764 A | 10/1994 | Marinos et al. | |
| 5,486,675 A | 1/1996 | Taylor et al. | |
| 5,503,081 A | 4/1996 | Lindblom et al. | |
| 5,665,277 A * | 9/1997 | Johnson et al. | 264/6 |
| 5,688,417 A | 11/1997 | Cadre et al. | |
| 5,770,022 A | 6/1998 | Chang et al. | |
| 5,788,738 A * | 8/1998 | Pirzada et al. | 75/331 |
| 5,874,134 A * | 2/1999 | Rao et al. | 427/446 |
| 5,876,683 A | 3/1999 | Glumac et al. | |
| 5,905,000 A * | 5/1999 | Yadav et al. | 429/33 |
| 5,935,461 A | 8/1999 | Witherspoon et al. | |
| 6,132,563 A | 10/2000 | Frach et al. | |
| 6,468,497 B1 * | 10/2002 | Khan et al. | 423/606 |
| 6,600,127 B1 | 7/2003 | Peterson et al. | |
| 6,689,192 B1 * | 2/2004 | Phillips et al. | 75/342 |

* cited by examiner

*Primary Examiner*—Stephen J. Kalafut
(74) *Attorney, Agent, or Firm*—Stuart T. Langley; Kent A. Lembke; Hogan & Hartson LLP (57) ABSTRACT

Methods to manufacture nanoscale particles comprising metals, alloys, intermetallics, ceramics are disclosed. The thermal energy is provided by plasma, internal energy, heat of reaction, microwave, electromagnetic, direct electric arc, pulsed electric arc and/or nuclear. The process is operated at some stage above 3000K and at high velocities. The invention can be utilized to prepare nanopowders for nanostructured products and devices such as ion conducting solid electrolytes for a wide range of applications, including sensors, oxygen pumps, fuel cells, batteries, electrosynthesis reactors and catalytic membranes.

48 Claims, 8 Drawing Sheets

NANOSTRUCTURED POWDERS AND RELATED NANOTECHNOLOGY

This application is a continuation of U.S. Ser. No. 09/988,901 entitled "Nanostructured Deposition and Devices", filed Nov. 19, 2001 now U.S. Pat. No. 6,610,355, which is a continuation of U.S. Ser. No. 09/251,313 entitled "Nanostructured Solid Electrolytes and devices, now issued as U.S. Pat. No. 6,387,560, filed on Feb. 17, 1999, which is a continuation of U.S. Ser. No. 08/739,257, entitled "Nanostructured Ion Conducting Solid Electrolytes", now issued as U.S. Pat. No. 5,905,000, filed Oct. 30, 1996, which is a continuation-in-part of U.S. Ser. No. 08/730,661, entitled "Passive Electronic Components from Nano-Precision Engineered Materials," filed on Oct. 11, 1996 now U.S. Pat. No. 5,952,040, which is a continuation-in-part of U.S. Ser. No. 08/706,819, entitled "Integrated Thermal Process and Apparatus for the Continuous Synthesis of Nanoscale Powders" filed Sep.03,1996 now issued as U.S. Pat. No. 5,851,507 on Dec. 22, 1998, and U.S. Ser. No. 08/707,341, entitled "Method Of Producing Nanoscale Powders By Quenching Of Vapors," filed concurrently on Sep. 3, 1996, now issued as U.S. Pat. No. 5,788,738 on Aug. 4, 1998. These applications and patents are all commonly owned with the present application, and are all incorporated by reference herein.

BACKGROUND OF THE INVENTION

1. Field of the Invention

This invention pertains in general to ion conductors and to processes for the synthesis of ion conducting solid electrolytes. In particular, the invention relates to the use of nanoscale powders for the preparation of nanostructured oxygen ion conducting electrolytes.

2. Description of the Prior Art

Solid electrolytes are materials through which ion species can migrate with low energy barriers. Table 1 outlines some examples of ion-conducting structures, representative materials, and the ions conducted. These materials are of critical commercial importance to electrochemical devices, components and processes. Illustrative applications include sensors, batteries, fuel cells, ion pumps, membrane reactors, catalysis, and metallurgy.

| REPRESENTATIVE MATERIALS | ION CONDUCTED |
|---|---|
| Stabilized $ZrO_2$ System, Stabilized $Bi_2O_3$ System, Ceria, Perovskites | $O^{2-}$ |
| Beta-Alumina, NASICON Systems | $Na^+$ |
| AgI, $RbAg_4I_5$ | $Ag^+$ |
| $Rb_4Cu_{16}I_7Cl_{13}$ | $Cu^+$ |
| $Li_3N$, $Li_2S$-$SiS_2$-$Li_3PO_4$ System, Organic Polymer Systems, LISICON Systems | $Li^+$ |

As a specific example, stabilized zirconia is a known conductor of oxygen ions. Accordingly, its properties are utilized in various fields of technology, such as in oxygen sensors for fuel-air ratio optimization of automobiles and furnaces, in oxygen pumps for solid state oxygen separation, in solid-oxide fuel cells for noiseless and clean power generation from chemical energy, and in catalytic membrane reactors.

The oxygen-ion conduction properties of stabilized zirconia used in a typical oxygen sensor are well understood based on electrochemical-cell theory. When placed between two compartments containing a reference gas and an analyte oxygen gas at different partial pressures, stabilized zirconia functions both as a partition between the two compartments and as an electrochemical-cell electrolyte. Under ideal conditions, the open-circuit emf ($E_0$) of the cell is given by the known Nernst equation:

$$E_0 = \frac{RT}{4F} \ln\left(\frac{PO_2^{Ref}}{PO_2}\right), \quad (1)$$

where T is the absolute temperature of the cell; $PO_2^{Ref}$ and $PO_2$ are the partial pressures of oxygen in the reference and analyte compartments, respectively; R is the universal gas constant; and F is Faraday's number.

According to this equation, any difference in partial pressure of the oxygen across the two faces of the oxygen-conducting electrolyte generates an electromotive force that depends on the temperature and partial-pressure ratio of the oxygen in the two compartments of the system. In order to generate Nernstian response in sufficiently short times, the temperature of stabilized $ZrO_2$ needs to be high (above 700° C.), which results in relatively high power requirements and in increased equipment mass and size, need for insulation, and attendant sealing problems. These considerations often produce unsatisfactory performance or affect the commercial viability of products based on stabilized $ZrO_2$ technology.

Figures 1A, 1B:
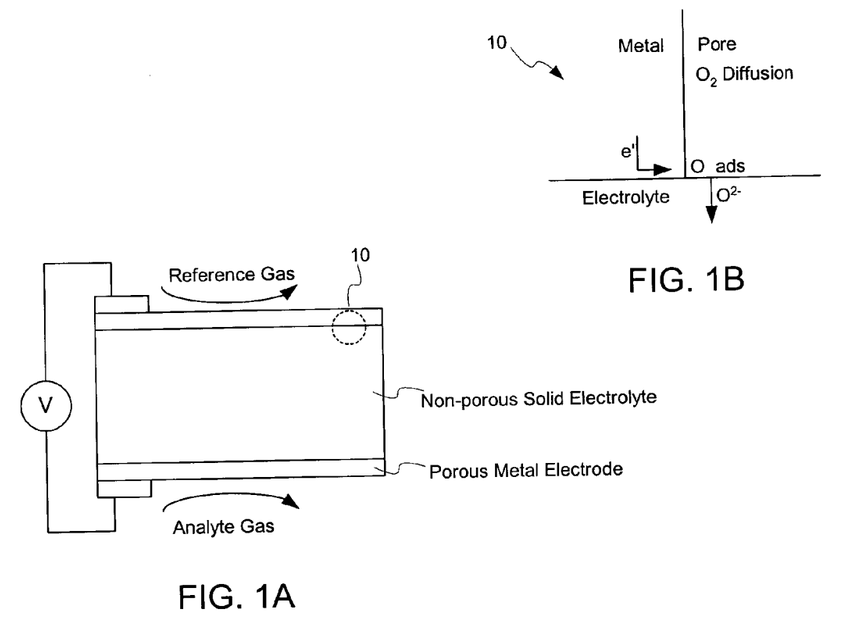
FIG. 1 is a schematic drawing of a $ZrO_2$ solid electrochemical cell where the stabilized zirconia is modeled as a solid electrolyte membrane sandwiched between a first compartment containing a reference oxygen atmosphere at a predetermined partial pressure and another compartment containing an analyte gas with oxygen at a different partial pressure.

The inherent reasons for the high-temperature requirement and the corresponding performance problems of present-day oxygen ion conducting electrolyte based devices can be traced to the reaction mechanism of the cell and the microstructure of the sites where the reaction occurs. Referring to FIG. 1A, a schematic drawing of a $ZrO_2$ sensor cell 10 is illustrated, where the stabilized zirconia is modeled as a solid electrolyte membrane 12 between a first compartment 14, containing a reference oxygen atmosphere at a predetermined partial pressure $PO_2^{Ref}$, and another compartment 16 containing an analyte gas with oxygen at a different partial pressure $PO_2$. The two sides of the stabilized zirconia non-porous solid electrolyte 12 are coupled through an external circuit connecting an anode 18 and a cathode 20 made of porous metal, such as silver. The anode 18 is the cell electrode at which chemical oxidation occurs and the electrons released by the oxidation reaction flow from it through the external circuit to the cathode. The cathode 20 is the cell electrode at which chemical reduction occurs. The cell electrolyte 12 completes the electrical circuit of the system by allowing a flow of negative ions $O^{2-}$ between the two electrodes. A voltmeter 22 is provided to measure the emf created by the redox reactions occurring at the interfaces of the electrolyte with the two oxygen atmospheres.

Thus, the key redox reaction of the cell occurs at the points where the metal electrode, the electrolyte and the gas meet (illustrated in the inset of FIG. 1 as the "triple point" 24). At each such site on the surface of the electrolyte 12, the redox reaction is as follows:

$$O_2 \text{ (gas)} + 4e^- \rightarrow 2O_2^{=} \quad (2)$$

Since the reaction and the electrochemical performance of the sensor depend on the redox kinetics, the cell's performance is a strong function of the concentration of triple points. In other words, an electrode/electrolyte/electrode cell with as many triple points as possible is highly desirable [see Madou, Marc and M. Morrison, *Chemical Sensing with Solid State Devices*, Academic Press, Boston (1989)]. In the case of an oxygen cell with a $ZrO_2$ solid membrane and silver electrodes, this requirement corresponds to maximizing the triple points on each side of the $PO^2 \cdot Ag'/ZrO_2/Ag''PO_2^{Ref}$ system.

Figure 2A:
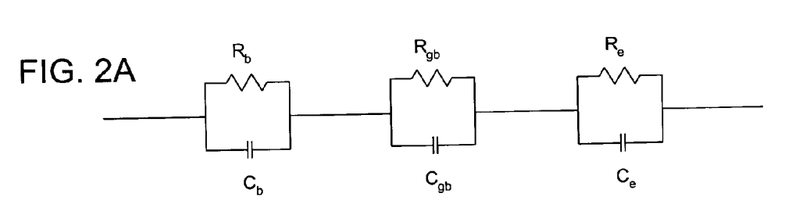
FIGS. 2a and 2b are a complex impedance diagram for a $ZrO_2$ sensor, where the impedances of the bulk, grain boundary and electrode are illustrated to reflect their contribution to the ionic conduction at each triple point shown in FIG. 1.
Figure 2B:
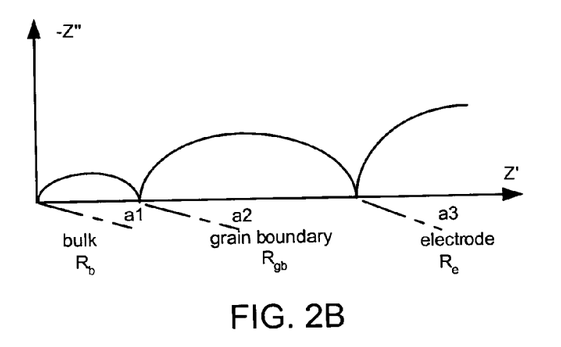

Another cause of poor performance of oxygen-sensor cells can be explained with the help of complex-impedance analysis. Referring to FIGS. 2a and 2b, a complex impedance diagram for a $ZrO_2$ sensor is shown, where the impedances of the bulk, grain boundary and electrode are illustrated in series to reflect their contribution to the ionic conduction at each triple point. It has been shown that the conductive performance of electrolytes at temperatures below 500° C. is controlled by the grain boundary contribution to the overall impedance. Thus, for significant improvements of the conductivity at low temperatures, it is necessary to significantly minimize the grain-boundary (interface) resistance.

In summary, oxygen ion conducting devices based on stabilized-zirconia electrolyte have two problems that can be traced to material limitations. First, the electrolytes have high impedance; second, the concentration of triple points is relatively low. These problems are common to solid oxygen-conducting electrolytes in particular and solid electrolytes in general, and any improvement in these material characteristics would constitute a significant technological step forward. The present invention provides a novel approach that greatly improves these aspects of ion conducting solid electrolytes.

SUMMARY OF THE INVENTION

One of the objectives of this invention is to enhance the ion-conductivity of solid electrolytes by preparing nanostructured solid electrolytes.

Another objective is to reduce the electrolyte thickness with the use of nanostructured precursors of solid electrolytes.

A further objective is to enhance the concentration of triple points in the ion conducting devices by using nanostructured precursors and materials.

Yet another objective of the invention is to utilize the unique properties of size confinement in solid electrolyte and electrode grains when the domain is confined to less than 100 nanometers.

Another objective of this invention is an oxygen-conducting electrolyte material with low-impedance oxygen conducting characteristics.

Another objective of the invention is an oxygen ion conducting device with a very high density of triple points.

Another goal is a process and materials that reduce the cost of manufacture of products that incorporate oxygen-ion conductors.

Yet another goal is a process and materials that reduce the cost of operation of products that incorporate oxygen-ion conductors.

Finally, another goal is a process that can be readily incorporated with conventional methods for manufacturing products containing ion-conducting electrolytes.

Various other purposes and advantages of the invention will become clear from its description in the specification that follows and from the novel features particularly pointed out in the appended claims. Therefore, to the accomplishment of the objectives described above, this invention comprises the features hereinafter illustrated in the drawings, fully described in the detailed description of the preferred embodiments and particularly pointed out in the claims. However, such drawings and description disclose only some of the various ways in which the invention may be practiced.

DETAILED DESCRIPTION OF THE INVENTION

This invention is based on the recognition that the ion conductivity of polycrystalline solid electrolytes at moderate and near-ambient temperatures is mainly controlled by the conductivity of grain boundary and the concentration of triple points. The invention further notes that the engineering of grain boundary resistance and triple points in solid electrolyte devices is limited by the electrolyte thickness and electrode characteristics, respectively, which in turn depend on grain size of the precursors and the material used in the manufacture of electrolytes and electrodes for solid ion conductors in general, and solid oxide oxygen sensors, solid oxide oxygen pumps and solid oxide fuel cells in particular. These limitations constitute an inherent obstacle to achieve significant technological improvements.

The finest powders currently available for commercial use consist of particles with sizes in the order of several microns. For example, the YSZ powders that are presently used to produce oxygen sensors have an average grain size of about 1 to 3 microns. Since the number of triple points occurring within a given area at the interface with the oxygen atmosphere is necessarily limited by the number of electrode grains distributed within that area, the grain size in the electrode is very important for maximizing redox-reaction sites. Similarly, since we know that the impedance of the system is reduced by electrolyte thickness, it follows that thinner electrolytes produced from smaller grains would produce lower impedance. Accordingly, the heart of this invention consists of using nanosize materials in the manufacture of electrolytes for these applications.

The current inability to improve the performance of solid ion conductors is a result of the inability of prior-art processes to economically reduce powder size of precursor materials beyond the micron-size range. Accordingly, the present invention is based on the work disclosed in commonly-owned U.S. Pat. Nos. 5,851,507 and 5,788,738 which provide a viable vehicle for manufacturing, nanoscale powders suitable for the present invention. Material having with physical properties as produced by the process and apparatus described therein is a necessary ingredient for practicing this invention on a commercial scale.

Manufacturing Nanoscale Powders

Figures 12, 13:
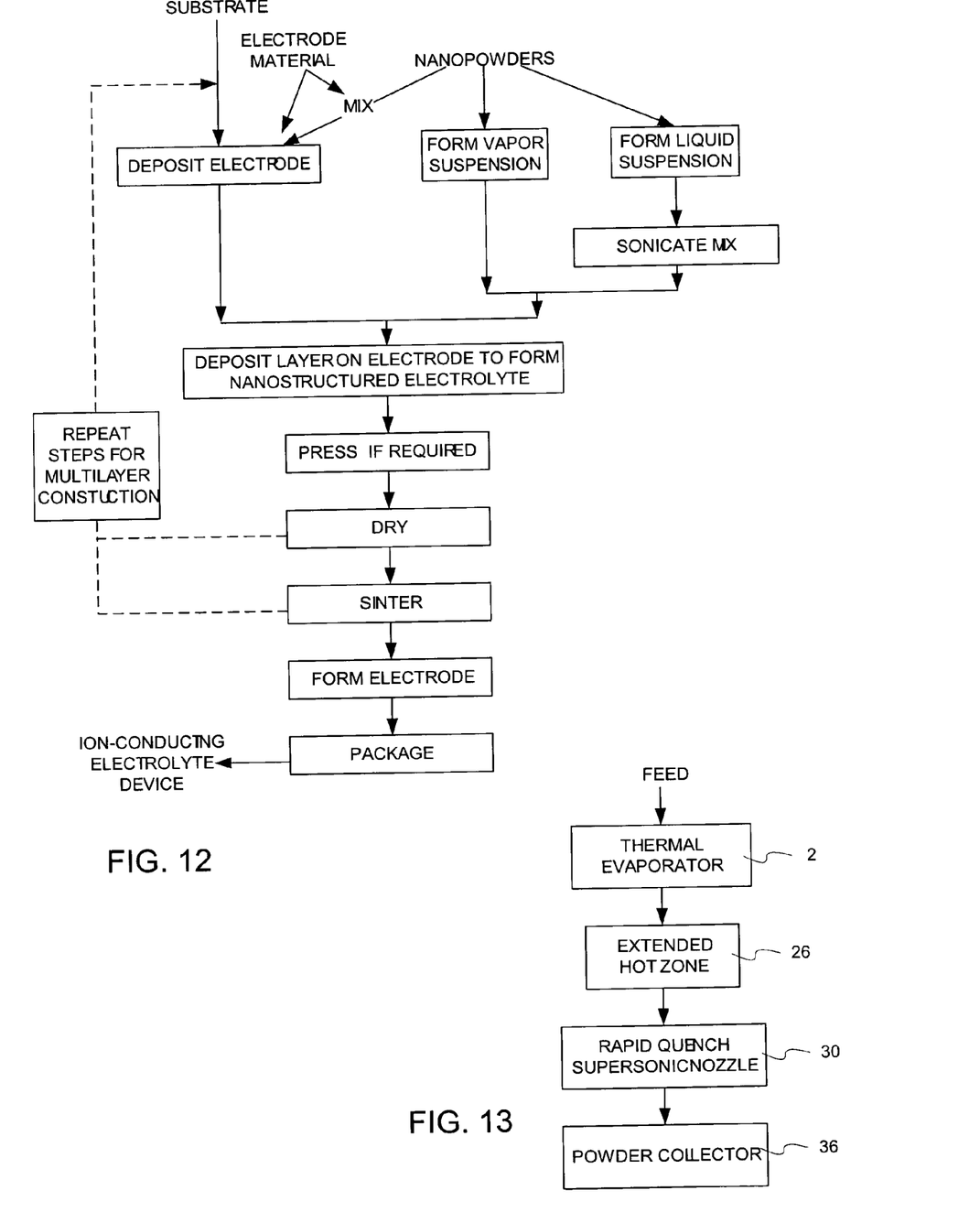
FIG. 12 is a flow diagram of the steps of deposition over a supporting substrate according to known vapor deposition processes applicable to the manufacture of nanostructured electrolytes according to the invention.
FIG. 13 is a block diagram of the thermal process of the present invention for the continuous synthesis of nanoscale powders.
Figure 14:
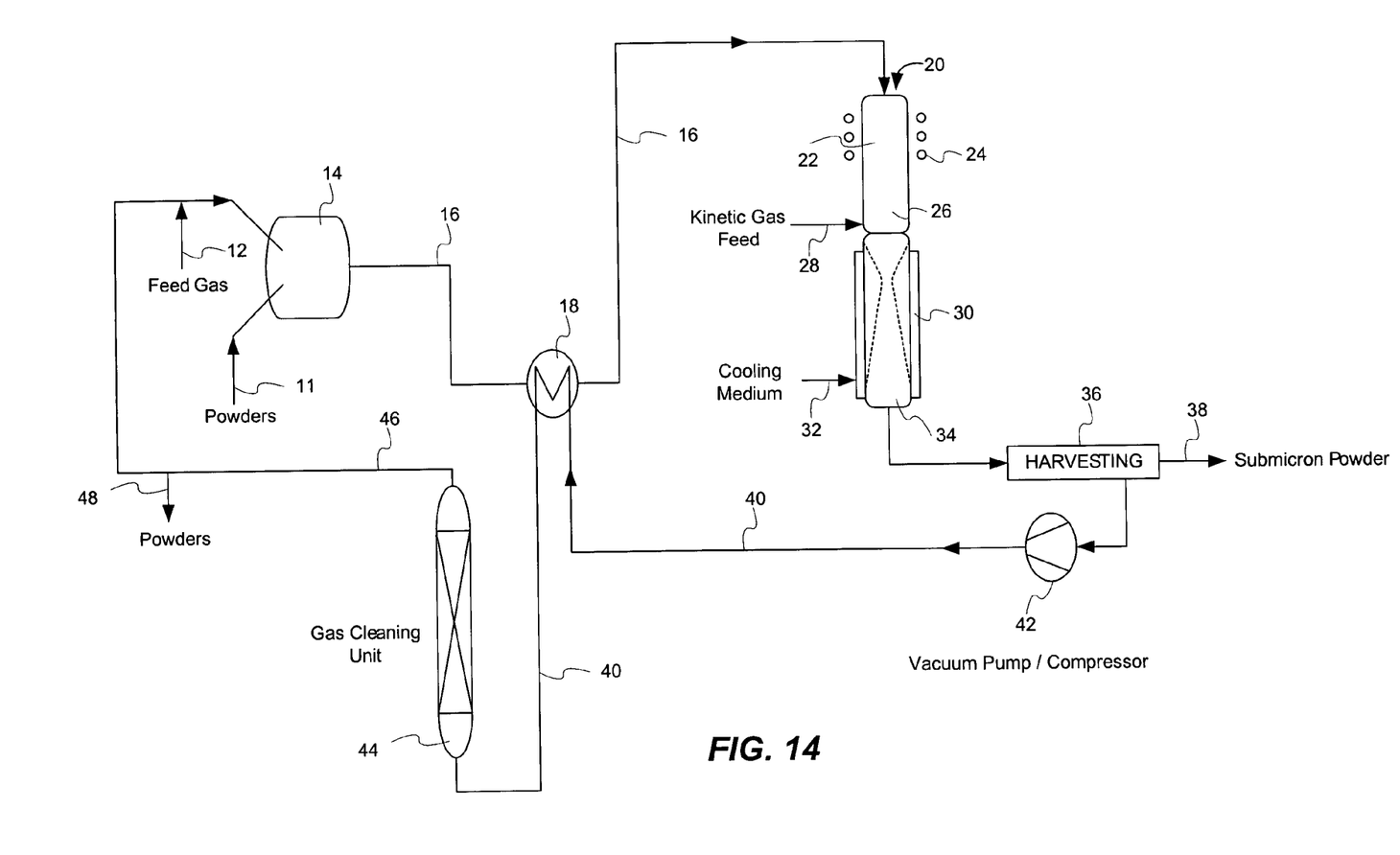
FIG. 14 is a schematic representation of the process for the continuous synthesis of nanoscale powders, including the adiabatic-expansion, thermal-quenching step of the invention.

As set out in U.S. Pat. No. 5,788,738, which is incorporated by reference herein, FIGS. 13 and 14 show a block diagram and a schematic flow diagram, respectively, of a thermal process for the continuous synthesis of nanoscale powders as applied to solid precursors such as metals, alloys, ceramics, composites, and combinations thereof with particle size (normally greater than 1 micrometer) suitable for continuous vaporization in a gas stream.

A feed stream 11 of a precursor material in powder form is premixed with a feed gas stream 12 (such as argon, helium, nitrogen, oxygen, hydrogen, water vapor, methane, air, or a combination thereof, depending on the particular precursor being processed and the corresponding atmosphere—inert, oxidizing, or reducing—required for the process) in mixing apparatus 14 appropriate to create a suspension. The powder 11 is suspended in the gas 12, preferably in a continuous operation, using fluidized beds, spouting beds, hoppers, or combinations thereof, as best suited to the nature of the precursor. The resulting gas-stream suspension 16 is advantageously preheated in a heat exchanger 18 and then is fed into a thermal reactor 20 where the suspended powder particles are partially or, preferably, completely evaporated in a thermal evaporation zone 22 by the input of thermal energy. The source 24 of such thermal energy may be internal energy, heat of reaction, conductive, convective, radiative, inductive, microwave, electromagnetic, direct or pulsed electric arc, nuclear, or combinations thereof, so long as sufficient to cause the rapid vaporization of the powder suspension being processed. Optionally, in order to prevent contamination of the vapor stream caused by partial sublimation or vaporization of the thermal reactor's interior walls, they may be pre-coated with the same material being processed.

The vaporized gas-stream suspension next enters an extended reaction zone 26 of the thermal reactor that provides additional residence time, as needed to complete the evaporation of the feed material and to provide additional reaction time (if necessary). As the stream leaves the reactor, it passes through a zone 56 where the thermokinetic conditions favor the nucleation of solid powders from the vaporized precursor. These conditions are determined by calculating the supersaturation ratio and critical cluster size required to initiate nucleation. Rapid quenching leads to high supersaturation which gives rise to homogeneous nucleation.

Using titanium powder as an example, based on the physical properties of the feed material and operating conditions in the reactor (size=10 microns, melting point=1, 660.degree. C., boiling point=3,287.degree. C., heat of vaporization of titanium=10.985 Btu/g, hot gas temperature=4,000.degree. C.), it is possible to calculate the residence time required for vaporization (2.32 msec for heating to melting point, 0.265 msec for melting, 5.24 msec for vaporization; total time required=8–10 msec). Based on the velocity of the suspension injected into the reactor and the travel distance through the reactor, one can determine that a velocity of about 46 ft/sec produces a residence time of 10.7 msec, sufficient for vaporization. If the process requires a predetermined thermokinetic state of the powder being processed which can be enhanced by the presence of a particular gas, a kinetic gas feed 28 (such as argon, helium, nitrogen, oxygen, hydrogen, water vapor, methane, air, or combinations thereof) can also be mixed with the precursor vapor to reach the desired thermokinetic state. As soon as the vapor has begun nucleation, the process stream is quenched in a converging-diverging nozzle-driven adiabatic expansion chamber 30 at rates at least exceeding 1000 K/sec, preferably greater than 1000000 K/sec, or as high as possible. As further detailed below, a cooling medium 32 is utilized for the converging-diverging nozzle to prevent contamination of the product and damage to the expansion chamber 30. Rapid quenching ensures that the powder produced is homogeneous, its size is uniform and the mean powder size remains in submicron scale.

The quenched gas stream 34 is filtered in appropriate separation equipment 36 to remove the submicron powder product 38 from the gas stream. As well understood in the art, the filtration can be accomplished by single stage or multistage impingement filters, electrostatic filters, screen filters, fabric filters, cyclones, scrubbers, magnetic filters, or combinations thereof. The filtered nanopowder product 38 is then harvested from the filter 36 either in batch mode or continuously using screw conveyors or gas-phase solid transport and the product stream is conveyed to powder processing or packaging unit operations (not shown in the drawings). The filtered gas stream 40 is compressed in a vacuum-pump/compressor unit 42 and cooled by preheating the gas-stream suspension 16 in heat exchanger 18. Thus, the enthalpy of compression can be utilized by the process as process heat through heat integration. Stream 40 is then treated in a gas cleaning unit 44 to remove impurities and any undesirable process product gases (such as CO, $CO_2$, $H_2O$, HCl, $NH_3$, etc). The gas treatment can be accomplished by single stage or multistage gas-gas separation unit operations such as absorption, adsorption, extraction, condensation, membrane separation, fractional diffusion, reactive separation, fractional separation, and combinations thereof. Finally, the treated gases 46 are recycled back to be reused with the feed gas stream 12. A small split stream 48 of the compressed treated gas 46 is purged to ensure steady state operation of the continuous thermal process.

Figure 3:
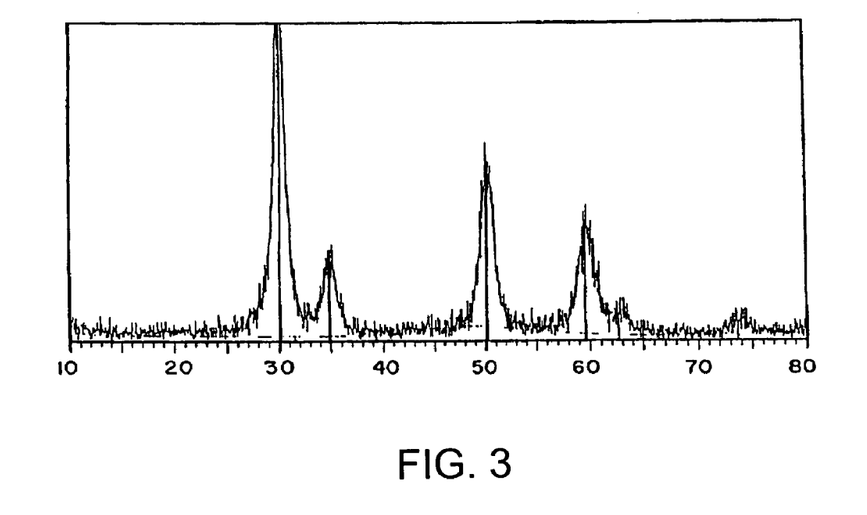
FIG. 3 is an X-ray diffraction pattern of the nanoscale yttria stabilized zirconia precursor used to form an electrolyte membrane according to the invention.

The invention was reduced to practice in a pilot plant illustrated schematically in FIG. 3. This thermal reactor system consists of an upper, cylindrical, thermal evaporation chamber 22 made of quartz and cooled by circulating water (not shown). The gas-stream suspension 16 is formed by mixing the solid feed material 10 fed by a powder feeder 11 with an inert gas stream 12, such as argon. The suspension 16 is injected continuously from the top of the thermal evaporation chamber 22 through a water-cooled injection probe 23 and is heated inductively by means of an RF plasma torch 24 (consisting of a plasma-gas source 25 and a suitable power supply 27). The reactor also comprises another, cylindrical, extended reaction zone 26 made of water-cooled stainless steel, positioned downstream of the thermal evaporation zone 22 and sufficiently large to provide the vaporized stream with the residence time required to complete the vaporization and reaction. The reaction zone 26 is lined with a zirconia refractory felt and a layer of silicon-carbide refractory material to reduce heat losses from the hot reaction zone. If necessary to prevent contamination of the reacting fluid by the reactor or refractory material, the reactor's interior walls (and refractory lining) may be further lined with the same material constituting the solid feed.

Figure 4:
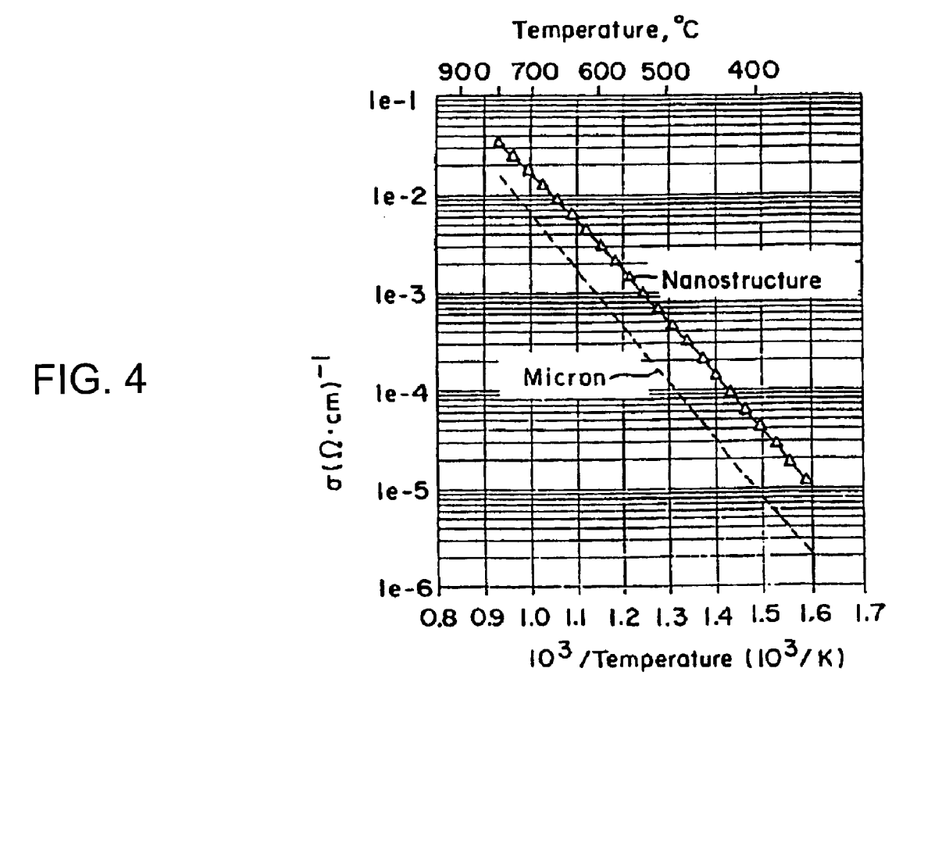
FIG. 4 is a graph of total conductivity versus temperature of 9-YFSZ nanozirconia prepared by the process of Example 1 and micron-based YFSZ material.

The adiabatic expansion chamber 30 consists of a Joule-Thompson converging-diverging nozzle (also known as a deLaval nozzle) having uniformly converging and diverging sections, as also illustrated in detail in FIG. 4. The nozzle is operated with a pressure drop (created by the vacuum pump 42 operated at least 50 Torr, normally between 100 and 650 Torr) sufficient for quenching the high-temperature vapors produced upstream in the reactor by plasma induction. The separation system 36 of the invention is realized by means of a collection chamber 35, attached to the outlet of the expansion chamber 30, where the very fine particles entrained in the gaseous stream are collected on a water-cooled metallic coil 37 (copper was used successfully for the test runs detailed below) and periodically extracted. It is anticipated that commercial-scale equipment would incorporate a screw or similar conveyor for the continuous removal of the nanopowder product from the collection chamber 35. The gas stream 40 out of the collection chamber is further passed through a filter 39 and trap 41 to thoroughly clean it prior to passage through the vacuum pump 42. A monitor and fluid-control panel 43 is utilized to monitor process variables (temperatures, pressures, water and gas flow rates), record them, and control all water and gas streams to maintain steady-state operation. It is noted that for simplicity the gas stream 48 exhausted from the vacuum pump 42 was not recycled in the demonstration plant of FIG. 3, but a commercial application would preferably do so for energy and material conservation.

In a continuous, steady-state process, the quench rate can be changed by changing the rate of expansion, which provides a much-sought form of control over the nucleation process of nanopowders produced by vapor condensation. Since it is known that the size, size distribution and other properties of vapor condensation products depend on the speed at which the nucleating material is quenched, the adiabatic expansion approach of the present invention provides an invaluable tool, missing in all prior-art processes, for controlling the quality of the resulting nanopowders. In addition, because the process can be carried out stably in continuous fashion, it provides a suitable vehicle for large scale applications and commercial production of bulk nanomaterials.

FIG. 5a is a sketch of a converging-diverging nozzle 50 to illustrate the relationship between critical parameters of the process and of the nozzle used to carry out the invention. It consists of an optimally-shaped combination of a convergent section 52, a throat section 54, and a divergent section 56. At steady state, the condensing fluid is restricted through a uniformly decreasing cross-section A.sub.1 from an initial cross-section A.sub.1 at pressure $P_1$ and temperature T1, it is passed through the cross-section A* of the throat 54, and then it is expanded through a final cross-section A.sub.2 at pressure P2 and temperature T2. The process is carried out through a cross-section A that is first uniformly decreasing and then uniformly increasing through the device. In the converging section 52, the Mach number M for the nozzle is less than 1, while it is equal to 1 in the throat 54, and greater than 1 in the diverging section 56. (Mach number is defined as the ratio of the hydrodynamic flow velocity to the local speed of sound.) Therefore, the initial subsonic flow is accelerated in the converging section of the nozzle, and the flow expands supersonically in the divergent section of the nozzle. At any cross-section A, the Mach number is given by the local value of A/A*, with m=1 at the throat.

Preparing Nanostructured Devices

As defined in the art, submicron powders are materials having average grain size below 1 micrometer. Of critical interest for this invention are nanoscale powders and nanostructured layers of ceramics and electrodes. Nanoscale powders (nanopowders) are submicron powders with average grain size less than 100 nanometers (preferably with a standard deviation of less than about 25 nm) and with a significant fraction of interfacial atoms. Accordingly, reference to nanoscale powders in this disclosure is intended to refer to powders with those characteristics.

Submicron layers are layers having thickness less than 1 micrometer. Of particular interest to this invention are nanostructured layers which are defined specifically as layers with thickness, or microstructure, or both, confined to a size less than property confinement size (positively less than 1 micron, preferably below 100 nm). Accordingly, reference to nanostructured layers in this disclosure is also intended to refer to layers with those characteristics.

As discussed in the copending applications, it is known that within these size ranges a variety of confinement effects occur that dramatically change the properties of the material. The idea of this invention then is to build ion conducting solid electrolytes from powders whose grain size has been confined to dimensions less than 100 nanometers. The size confinement effects in nanometer scale can confine fundamental processes to band-gap and quantum confined states which in turn can dramatically change the properties and performance of the resulting solid electrolyte. This insight can be implemented as devices prepared with one dimensional quantum dot and nanocluster composite with the dot size less than 100 m (preferably less than 10 nm), as quantum wires with diameter less than 100 nm (preferably less than 10 nm), as quantized and nanoscale films with film thickness less than 100 nm, as nanostructured layers and pellets with microstructure less than 100 nm, and as a combination of these. In summary, another aspect of the invention concerns the preparation of solid electrolyte and electrodes that are nanostructured.

Nanostructured ion conducting electrolytes prepared from nanostructured materials have grain sizes spatially confined to less than 100 nanometers; a significant fraction (20–60%) of their atoms is interfacial, and exceptional interactions occur between the constituent domains. Therefore, nanostructured oxygen-conducting electrolytes can be expected to have very high concentrations of interface area which can assist rapid and low-temperature densification of ion conducting electrolytes. The nanoscale powder can also enable dramatic reduction in layer thicknesses as discussed in co-pending applications. Furthermore, since nanostructure provides higher density of surface area, the density of triple points at the electrolyte-electrode-gas interface can also be significantly enhanced using nanostructured-electrolyte/electrode interactions. Given low resistance and high triple-point concentration, nanostructured electrolytes and electrodes can be used to achieve higher ion conductivity and electrochemical activity. This is of particular interest when an ion conducting device has to operate at near ambient temperatures. This general design principle is applicable to all, solid ion conductors based on ion defect structure, two dimensional layered structure, three dimensional network structure, vitreous structure, $\alpha$-AgI type structure, and composites prepared using these structures. Illustrative examples include, without limitation, oxide ion conductors such as stabilized zirconia, stabilized ceria, stabilized bismuth oxide, perovskites, LISICON, NASICON, and $\beta$-alumina.

The following examples illustrate different ways of reducing the present invention to practice.

EXAMPLE 1

A stock solution was prepared from $ZrOCl_2.8H_2O$ and 9 mol % $Y_2O_3$ in water, and diluted with denatured ethanol. The solution was chilled to 0° C. and then slowly added to a continuously stirred basic solution of ammonium hydroxide that was also maintained at 0° C. Precipitation of white precursor powder was instantaneous. The precipitate solution was suction filtered, and the gelatinous filter cake was washed in denatured ethanol three times. The loose powder so generated was dried quickly with mild heating at 100° C. to remove water and ethanol, and calcined to 500° C. in air to form nanocrystallites with grain size of about 5.8 nm, standard deviation of 1.1 nm. This precursor material consisting of 9 mole-percent yttria stabilized zirconia (YSZ) nanoscale powders was examined using, an X-ray diffractometer (XRD). A typical XRD pattern for the 9 mole powders so produced is illustrated in FIG. 3, which shows that the $ZrO_2$ is stabilized cubic phase. In order to determine the average particle size of the powders, the widths of strong, low order peaks of XRD pattern were analyzed using Scherrer's method. The average particle size of the powders according to this analysis was found to be about 4.5 nanometers. The particle size was also verified by transmission electron microscopy (TEM). The results suggested a particle size of 5.8 nanometers.

The nanoscale 9 mole % yttria stabilized cubic zirconia powders were pressed into 3 mm diameter discs (0.15 gram weight) and sintered to high densities (preferably more than 90% of theoretical density for mechanical strength, over 95% being preferred). The sample disks were sintered at low temperatures (1,150 to 1,250° C., yielding more than 95% density) and for short duration (6 to 24 hours) to minimize grain growth. We found that YSZ nanopowders readily sintered to full theoretical densities at about 1,200° C. in 17 hours, which represent significantly milder and less expensive processing conditions than presently necessary. Careful control of the sintering profile and time can further reduce the sintering temperature and time. The cylindrical discs were examined under XRD and the post-sintered mean grain size by Scherrer analysis was found to be about 83 nm, confirming that the discs were nanostructured. The two ends of the cylindrical discs so produced were then coated with a cermet paste consisting of a mix of silver and nanoscale yttria stabilized zirconia powder (about a 50–50 wt % mix, corresponding to a 35Ag–65YSZ vol % mix). Then platinum leads were attached to the cermet layer.

Figure 5:
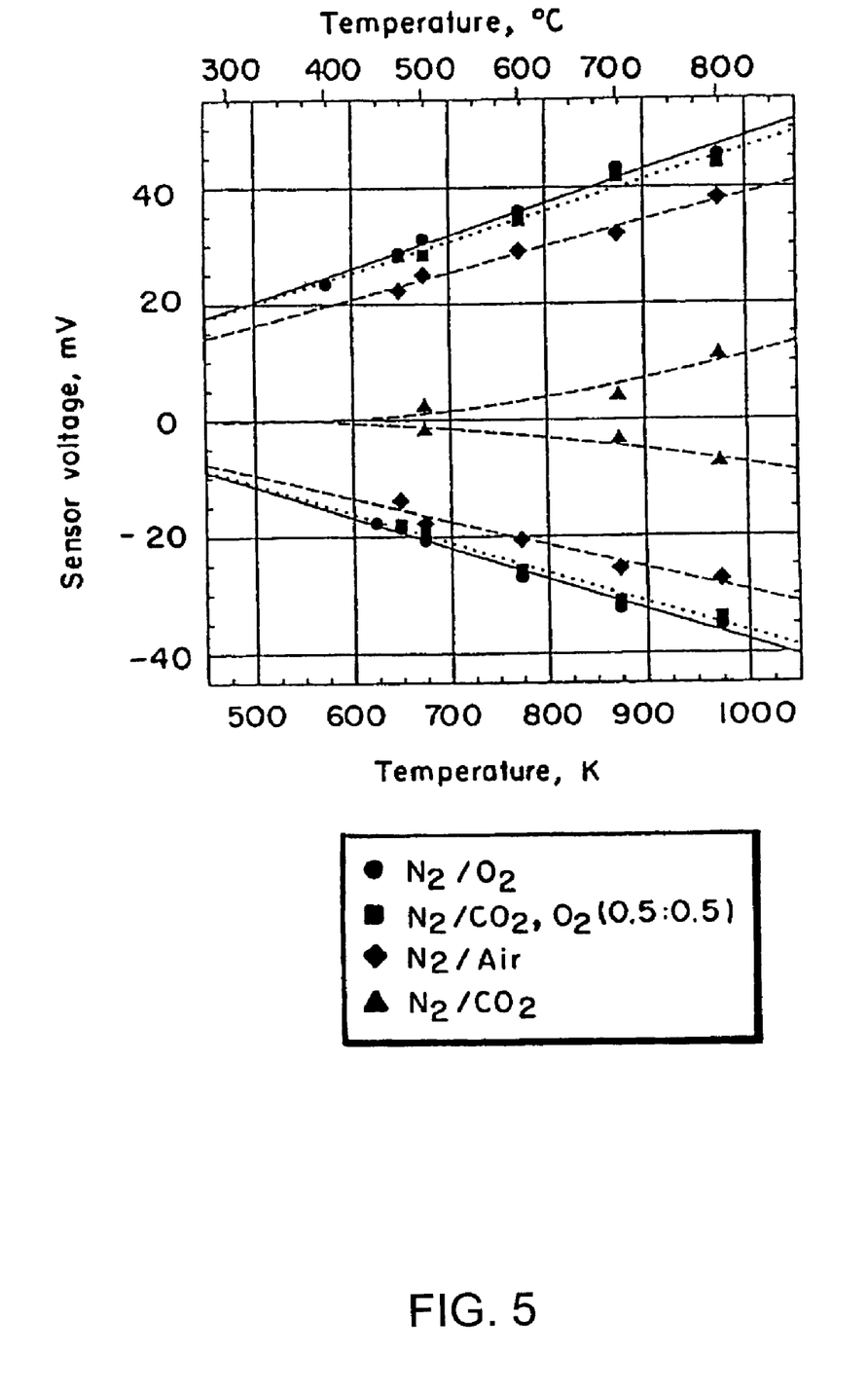
FIG. 5 is a voltage-versus-temperature graph of a nanostructured oxygen sensor manufactured with the material prepared in Example 1. The symmetrical response about the abscissa relates to switching the gases from one face of the sensor to the other.

The samples were placed in a furnace and their impedance was measured in air as a function of increasing temperature with a computerized impedance analyzer. A standard 40 mV AC bias and frequency sweep range of 5 Hz to 13 MHz were used. As illustrated in FIG. 5, the results so obtained suggest that nanostructured oxygen-conducting electrolytes, referenced by n, exhibit almost an order of magnitude higher oxygen-ion conductivities at lower temperatures when compared with base-line electrolytes, referenced by $\mu$ (i.e., conventional micron-powder based oxygen-conducting electrolytes). It is noted that neither the baseline nor the nanostructured electrolytes represent optimal performance. For additional electrochemical and electrocatalytic performance evaluation, the Ag/YSZ/Ag cell was tested as a sensor and oxygen pump. For sensor/fuel-cell experiments, oxygen containing gas was passed over one face of the sensor and nitrogen was passed over the other face of the sensor. The emf response as a function of temperature was measured. As shown in FIG. 5, the results indicate that the sensor signal for each gas combination is linear with temperature, confirming a Nernst-type behavior. For electrosynthetic oxygen generation and pumping applications, $CO_2$ was passed over one face while nitrogen was passed over the other face. FIG. 5 shows that the oxygen-conducting electrolyte exhibited oxygen pumping properties at low temperatures.

EXAMPLE 2

Figure 6:
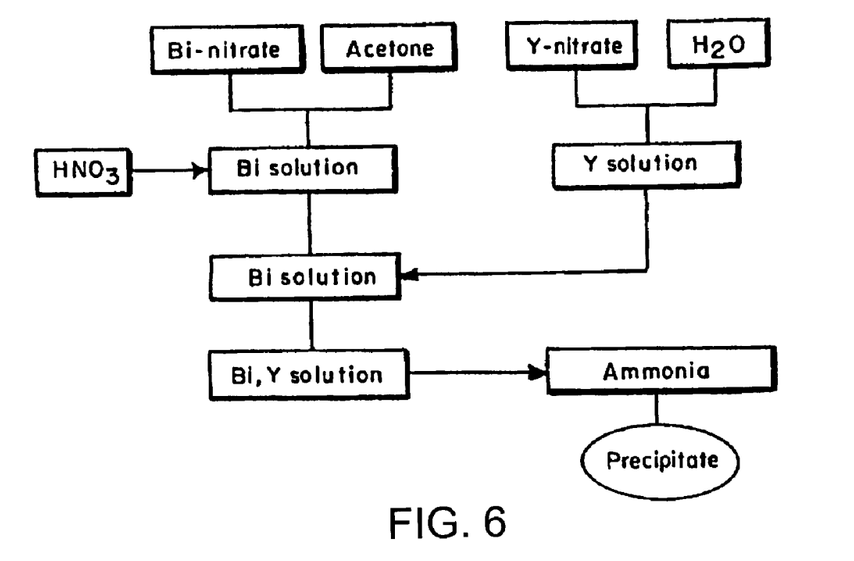
FIG. 6 is a flow chart of the process for preparing a yttria stabilized bismuth oxide (YSB) nanopowder from nitrates by a solution method.
Figure 7:
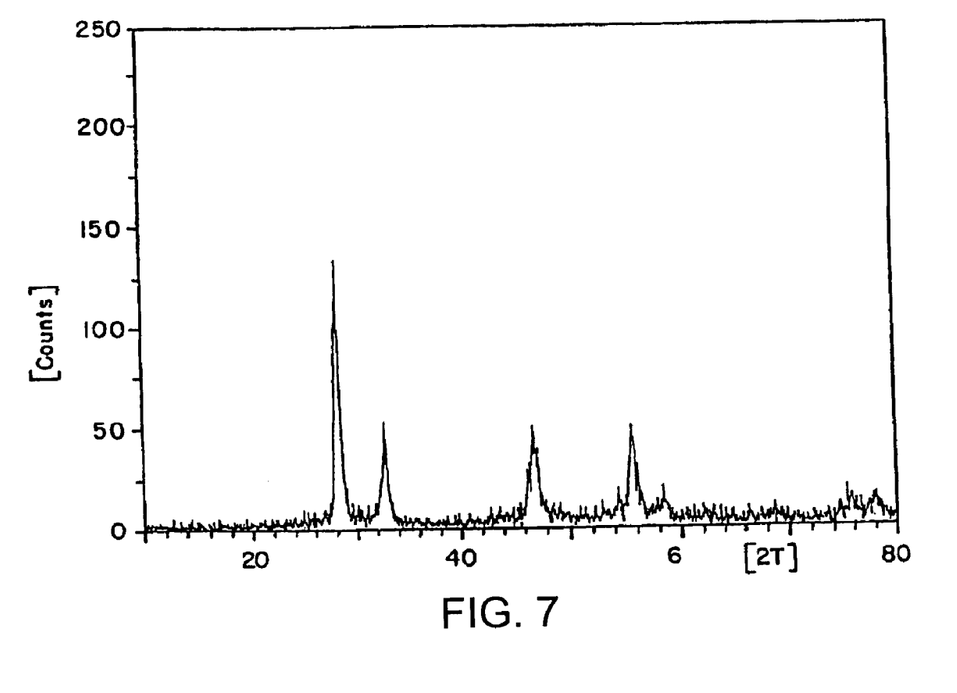
FIG. 7 is an X-ray diffraction pattern of the nanostructured YSB product of Example 2.

Bismuth nitrate $(Bi(NO_3)_3.5H_2O)$ and yttrium nitrate $(Y(NO_3).6H_2O)$, were used as precursors for preparing nanosized yttria stabilized bismuth oxide (YSB) powder via solution co-precipitation. FIG. 6 shows a flow chart of the co-precipitation processing steps used in this example. After precipitation, the precipitate solution was suction filtered, and the gelatinous filter cake was washed in acetone to minimize agglomeration of ultrafine powder due to hydrogen bonding. The loose powder so generated was next dried with mild heating to remove water and acetone. Then the powder was calcined in air at 500° C. for 2 hours. XRD showed that calcine schedule resulted in a single cubic YSB phase (see FIG. 7). The volume averaged crystallite size of the powder fired at 500° C. was determined to be 12.5 nm by analyzing the broadening of the (111) diffraction peak and applying Scherrer's formula. The YSB nanopowder was characterized in terms of morphology and particle size by transmission electron microscopy (TEM). The average particle size was estimated to be about 15 nm, which is in good agreement with the result obtained from XRD analysis.

The nanopowders were uniaxially pressed at 50,000 psi into green pellets of 12.5 mm in diameter and 1 mm in thickness. The pressing process consisted of initially lubricating the die with a die lube, followed by the weighing of an appropriate amount of powder, inserting the powder in the die, uniaxially pressing to the desired pressure, holding at that pressure for 30 seconds, and then slowly releasing the pressure over 15 seconds. Subsequently, the pellet was forced out from the die. No binder was added for the forming, process. It was found that from the nanopowder the electrolytes can be sintered with greater than 96% of theoretical density at temperatures ranging from 850 to 950° C. In contrast, YSB electrolytes made from micron-sized powder are typically sintered at temperatures greater than 1,000° C. It is known that the primary driving force for densification of ceramics is the reduction of free surface area at high temperatures. The very small size of the YSB nanopowder, therefore, has a very large driving force for densification; thus, the required sintering temperature can be significantly reduced relative to commonly used micron-sized powders. This is an important manufacturing advantage of this invention.

The concept of the invention is also applicable to improve the performance of electrodes for ion conducting materials. These electrodes should have high electrical conductivities, high catalytic activities, adequate porosity for gas transport, good compatibility with the electrolyte, and long-term stability. In order to achieve high catalytic activities, it is preferred that the electrode be highly porous, so that it retains a large number of active sites for electrochemical reactions, i.e., the triple points. Ag has been studied as an electrode material because it is known to have high electrical conductivity and high catalytic activity for oxygen reduction and evolution. However, pure Ag electrodes readily densify during processing and operation, resulting in a dense electrode with little porosity. In order to reduce the electrode resistance, the teachings of this invention were used to prepare nanocomposite electrodes from Ag and nanostructured powders of the ion electrolyte material.

EXAMPLE 3

YSB electrolyte pellets, 19 mm in diameter and 0.9 mm in thickness, were sintered from green pellets of 25 mm in diameter and 1.2 mm in thickness. The pellets were ground and polished to a thickness of 0.7 mm to provide a suitable electrolyte substrate. A separate composite paste of 79 vol % Ag and 21 vol % YSB was prepared by mixing nanopowder of YSB and unfritted Ag paste (marketed by the Cermalloy Division of Heraeus Incorporated of West Conshohocken, Pa., under Catalog No. C440OUF). The paste was printed onto both sides of the pellet to form electrodes, and then the pellet was fired at 800° C. for 10 minutes to sinter the electrolyte without densifying it beyond the point necessary to provide a robust structure and form a stabilized sensor cell with porous composite electrodes (about 18% porosity). Then Ag wire was attached to both electrodes with a contact of Ag epoxy which was fired at 730° C. for 2 minutes. It is noted that the composite-electrode/electrolyte structure needs to be stabilized by the application of heat, pressure or chemical action, as the particular composition of the composite constituents may require or allow, in order to provide a physically robust and stable product.

In the resulting composite electrode structure, we found that the densification of the Ag_phase is inhibited by the ion electrolyte material phase. The electrodes then retain a porous microstructure during and after thermally demanding processing and operation. The retained porous microstructure significantly enhances the performance of the electrodes. In addition, electrodes of this kind have better adhesion to the electrolytes because the stress arising from thermal expansion mismatch between the ceramic electrolyte and the metal electrode is minimized not only by the porous, heterogeneous microstructure of the electrodes but also by tailoring the thermal expansion coefficient of the nanocomposites. We found that a nanostructured electrode composite sintered to 50–85 percent of full theoretical density (i.e., producing an electrode composite with 15–50 percent porosity) is optimal to obtain these advantages of performance.

Figure 8:
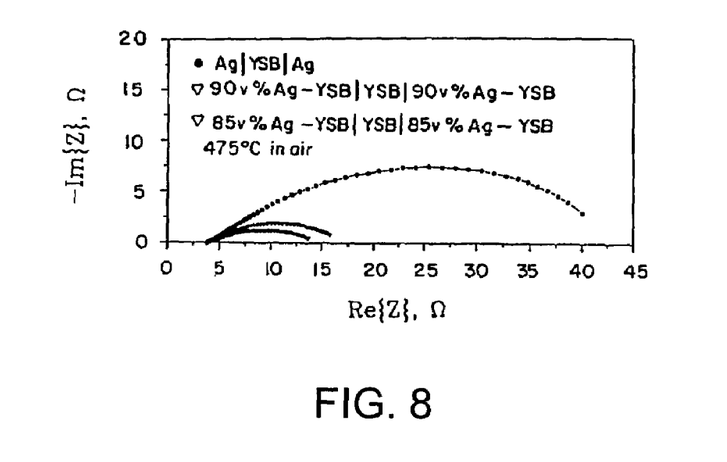
FIG. 8 illustrates Nyquist plots of impedance spectra of cells with the nanocomposite electrodes of Example 3 in comparison with a cell with pure Ag electrodes.

Further, another important advantage is derived from using nanocomposite electrodes. If the phases added are ionic conductors or mixed electronic-ionic conductors, the nanocomposite electrode as a whole turns out to be a mixed conductor, which allows ambipolar transport within the solid phase. FIG. 8 illustrates Nyquist plots of impedance spectra of cells with the nanocomposite electrodes in comparison with a cell with pure Ag electrodes. As determined from the impedance spectra, the polarization resistances of the nanocomposite electrodes are significantly smaller than that of the pure Ag electrode. As expected, the resistance of the nanocomposite electrode is a function of the composition, i.e., the volume fraction of each constituent phase. This allows much room for performance optimization by adjusting the composition of the composites. The nanocomposite electrode shows a nearly 4-fold reduction in electrode resistance as compared to the pure Ag electrode. We found that good results are obtained with a mix of 0 to about 65 vol % electrolyte (35 to 100 vol % metallic electrode material), the limit being that a continuum metal phase must exist for a viable porous electrode structure. That is, the amount of electrolyte must not be so great as to cause interruptions in the connectivity of the metal phase. At least 5 vol % electrolyte, 21 vol % being preferred, produced good results with different metal/electrolyte combinations. We believe that with composition optimization, further reduction in electrode resistance can be achieved, leading to a significant enhancement in ion conducting device's performance.

A sensor produced with the structure manufactured in Example 3 was operated in the following configuration, using air as the reference gas:

air, 79v %Ag21v %YSB|YSB|79v %Ag21v %YSB,
Analyte gas.

The sensor response to the changes in the gas composition and in temperature was monitored by measuring the cell voltage under different conditions.

Figure 9:
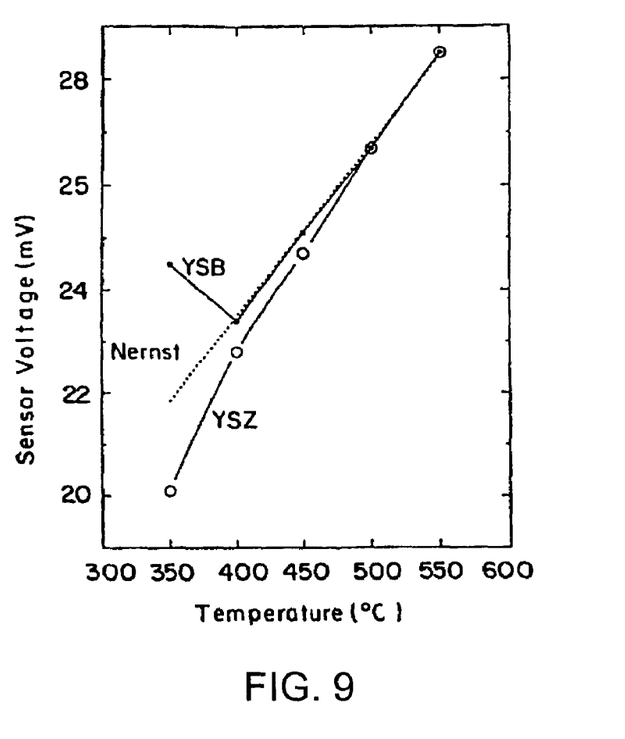
FIG. 9 is the voltage response in oxygen of the sensor of Example 3 as a function of temperature in comparison with that of a conventional YSZ sensor.

Shown in FIG. 9 is the sensor voltage response in oxygen as a function of temperature in comparison with that of a conventional YSZ sensor. FIG. 9 clearly shows that the response of the YSB sensor follows Nernst behavior down to 400° C., while the response of the YSZ sensor deviates from Nernst behavior below 500° C. This indicates that the YSB proof-of-concept sensor can be operated at a temperature about 100° C. lower than conventional YSZ sensors.

Figure 10:
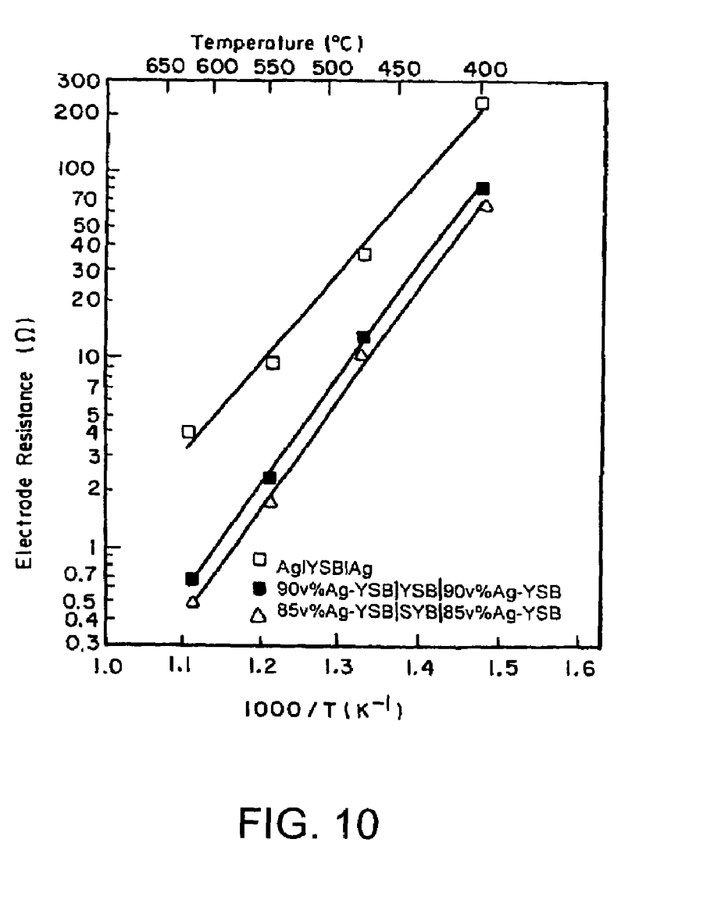
FIG. 10 shows electrode resistances of pure Ag electrode and nanocomposite electrodes as a function of temperature, as determined from the impedance spectra measured in air.
Figure 11:
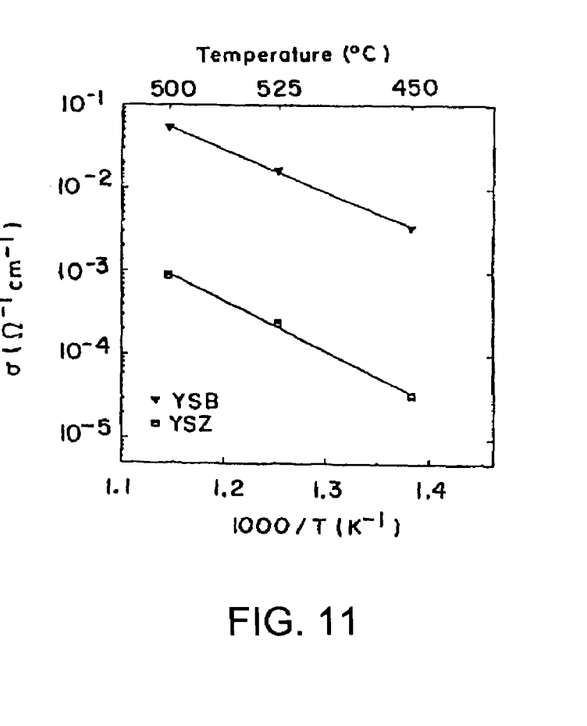
FIG. 11 shows a comparison of the ionic conductivity of nanostructured YSB electrolyte with YSZ electrolyte.

FIG. 10 further shows electrode resistances of nanocomposite electrodes as a function of temperature, as determined from the impedance spectra measured in air. Also shown in the figure are the data for pure Ag electrode for comparison. As compared with pure Ag electrode, the nanocomposite electrodes show significantly lower resistances. The ionic conductivity of the nanostructured YSB electrolyte was measured and found to be over two orders of magnitude higher than that of YSZ electrolyte, as shown in FIG. 11.

The impedance measurements and the data shown in these examples establish that nanostructured solid ion electrolytes and electrodes are indeed significantly superior in performance to solid ion electrolytes and electrodes prepared from micron-sized powders. The invention reduced to practice the use of nanostructured ion-conducting electrolytes exhibiting ion conductivity higher than obtained by prior-art technology; and it demonstrated the successful fabrication of ion-conducting electrolytes in general, and oxygen-conducting electrolytes in particular, from materials with grain size less than 100 nm for electrochemical, electrosynthesis and electrocatalytic applications. It is noted that the methods of assembly or deposition of nanoparticles to form structures according to this invention may vary depending on the particular application. For example, dry particles may be pressed into a structure of predetermined geometry, as illustrated in Example 1, or deposited over a supporting substrate according to known vapor deposition processes, as described in copending Ser. No. 08/730,661 and illustrated in FIG. 12.

EXAMPLE 4

Zinc

Commercially available zinc powder (−325 mesh) was used as the precursor to produce nanosize zinc powder. Feed zinc powder was fed into the thermal reactor suspended in an argon stream (argon was used as the plasma gas; the total argon flow rate was 2.5 ft$^3$/min). The reactor was heated with 16 kW of plasma to over 5,000K in the plasma zone and about 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. After undergoing a pressure drop of 100 to 550 Torr through the converging-diverging nozzle, the powder produced was separated from the gas by means of a cooled copper-coil-based impact filter followed by a screen filter. The nanosize powder produced by the invention were in the 5–25 nanometer range. The size distribution was narrow, with a mean size of approximately 15 run and a standard deviation of about 7.5 nm.

EXAMPLE 5

Iron-Titanium Intermetallic

2–5 micron powders of iron and 10–25 micron powders of titanium were mixed in 1:1 molar ratio and fed into the thermal reactor suspended in an argon stream (total gas flow rate, including plasma gas, was 2.75 ft$^3$/min). The reactor was heated with 18 kW of plasma to over 5,000K in the plasma zone and above 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. After undergoing a pressure drop of 100 to 550 Torr through the converging-diverging nozzle, the powder produced was separated from the gas by means of a cooled copper-coil-based impact filter followed by a screen filter. The nanopowders produced by the invention were in the 10–45 nanometer range. The size distribution was narrow, with a mean size of approximately 32 nm and a standard deviation of about 13.3 nm.

EXAMPLE 6

Tungsten Oxide

Commercially available tungsten oxide powder (−325 mesh size) was used as the precursor to produce nanosize $WO_3$. The tungsten oxide powder was suspended in a mixture of argon and oxygen as the feed stream (flow rates were 2.25 ft$^3$/min for argon and 0.25 ft.sup.3/min for oxygen). The reactor was heated with 18 kW of plasma to over 5,000K in the plasma zone and about 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. After undergoing a pressure drop of 100 to 550 Torr through the converging-diverging nozzle, the powder produced was separated from the gas by means of a cooled copper-coil-based impact filter followed by a screen filter. The powder produced by the invention were in the 10–25 nanometer range. The size distribution was narrow, with a mean size of about 16.1 nm and a standard deviation of about 6.3 nm.

EXAMPLE 7

Cerium Oxide

Commercially available cerium oxide powder (5–10 micron size) was used as the precursor to produce nanosize $CeO_2$. The cerium oxide powder was suspended in a mixture of argon and oxygen as the feed stream (at total rates of 2.25 ft$^3$/min for argon and 0.25 ft$^3$/min for oxygen). The reactor was heated with 18 kW of plasma to over 5,000K in the plasma zone and about 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 650 Torr. The powder produced was separated from the gas by means of a cooled copper-coil-based impact filter followed by a screen filter. The powder produced by the invention was in the 5–25 nanometer range. The size distribution was narrow, with a mean size of about 18.6 nm and a standard deviation of about 5.8 nm.

EXAMPLE 8

Silicon Carbide

Commercially available silicon carbide powder (−325 mesh size) was used as the precursor to produce nanosize SiC. The powder was suspended in argon as the feed stream (total argon flow rate of 2.5 ft$^3$/min). The reactor was heated with 18 kW of plasma to over 5,000K in the plasma zone and about 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. The powder produced was separated from the gas by means of a cooled copper-coil-based impact filter followed by a screen filter. The SiC powder produced by the invention were in the 10–40 nanometer range. The size distribution was narrow, with a mean size of approximately 28 nm and a standard deviation of about 8.4 nm.

EXAMPLE 9

Molybdenum Nitride

Commercially available molybdenum oxide ($MoO_3$) powder (−325 mesh size) was used as the precursor to produce nanosize $Mo_2N$. Argon was used as the plasma gas at a feed rate of 2.5 ft$^3$/min. A mixture of ammonia and hydrogen was used as the reactant gases ($NH_3$ at 0.1 ft$^3$/min; $H_2$ at 0.1 ft$^3$/min). The reactor was heated with 18 kW of plasma to over 5,000K in the plasma zone and about 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. The powder produced was separated from the gas by means of a cooled copper-coil-based impact filter followed by a screen filter. The $Mo_2N$ powder produced by the invention was in the 5–30 nanometer range. The size distribution was narrow, with a mean size of about 14 nm and a standard deviation of about 4.6 nm.

EXAMPLE 10

Nickel Boride

10–50 micron powder of nickel boride were fed into the thermal reactor with argon (fed at a total rate, including plasma gas, of 2.75 ft$^3$/min). Once again, the reactor was heated with 18 kW of plasma to over 5,000K in the plasma zone and about 3,000K in the extended reactor zone adjacent the converging portion of the nozzle. The vaporized stream was quenched through the converging-diverging nozzle. The preferred pressure drop across the nozzle was 250 Torr, but useful results were obtained at different pressure drops, ranging from 100 to 550 Torr. The powder produced was separated from the gas by means of a cooled copper-coil-based impact filter followed by a screen filter. The $Ni_3B$ powder produced by the invention was in the 10 to 30 nanometer range. The size distribution was narrow, with a mean size of about 12.8 nm and a standard deviation of about 4.2 nm.

EXAMPLE 11

Reacting Feed

Oxide Ceramics: 5–10 micron powders of calcium carbonate were fed into the thermal reactor with argon (at 2.5 ft.sup.3/min). The reactor was heated with 16 kW of plasma to over 5,000K in the plasma zone and about 2,500K in the extended reactor zone adjacent the converging portion of the nozzle. The vaporized stream was quenched by thermal expansion to about 100 Torr. The pressure drop across the nozzle was 250 Torr, but useful results were obtained at different pressure drops, ranging from 50 to 550 Torr. The powder produced was separated from the gas by means of a cooled copper-coil-based impact filter followed by a screen filter. The TEM image of powder produced show it to be in the 5 to 20 nanometer range. As expected from the reaction occurring in the reactor, the XRD data established that the main phase of the nanopowder was CaO. The size distribution of the CaO was narrow, with a mean size of about 14.8 nm and standard deviation of about 3.8 nm.

An alternate run was made with $MgCO_3$ powders with mean size of about 7 microns processed with argon. Once again, nanoscale powders of MgO were produced as evidenced by TEM and XRD data. The final product powder size was observed to vary with changes in the pressure, temperature, flow rate, and compositions.

The process of deposition may also be incorporated with the process of manufacture of the nanosize particles disclosed in the referenced copending applications. This method is preferred because it enables the continuous fabrication of product from raw material. A thermal reactor system is used to produce nanoscale powders by ultra-rapid thermal quench processing of high-temperature vapors through a boundary-layer converging-diverging nozzle. A gas suspension of the micron-sized material is continuously fed to a thermal reaction chamber and vaporized under conditions that minimize superheating and favor nucleation of the resulting vapor. The high temperature vapor is quenched by passing the vapor stream through the nozzle immediately after the initial nucleation stages, thereby rapidly quenching it through expansion at rates of at least 1,000° C. per second, preferably greater than 1,000,000° C. per second, to block the continued growth of the nucleated particles and produce a nanosize powder suspension of narrow particle-size distribution. A gaseous boundary-layer stream is preferably also injected to form a blanket over the internal surface of the nozzle to prevent vapor condensation in the throat of the nozzle. A receiving substrate is placed in the diverging section of the nozzle to receive the nanoparticles produced in the quenched stream. Thus, a nanostructured layer of electrolyte material can be deposited directly as desired on the particular device being manufactured. As those skilled in the art would readily understand, the precise location of the substrate within the nozzle, the residence time, and other operating parameters could be manipulated to produce the physical structure desired for a particular application.

Potential applications of the invention include nanostructured solid electrolyte and electrode based devices for energy storage and generation such as, but not limiting to batteries, fuel cells, devices for thermodynamic property measurements; electrochemical sensors for monoatomic, diatomic and polyatomic gases such as, but not limiting to atomic oxygen found in atmosphere, diataomic oxygen and ozone sensors; ion sensors; oxygen pumps; solid state chemical pumps; monitors for steam electrolyzers; measurement of dissolved oxygen in liquid metals; measurement of pH; electrocatalysis, electrosynthesis, catalytic membrane reactors, and high-temperature kinetic studies. Therefore, while the present invention has been shown and described herein in what is believed to be the most practical and preferred embodiments, it is recognized that departures can be made therefrom within the scope of the invention, which is therefore not to be limited to the details disclosed herein but is to be accorded the full scope of the claims so as to embrace any and all equivalent apparatus and methods.

I claim:

1. A process for manufacturing nanoscale powders comprising:
   providing a feed comprising solid powders;
   providing thermal energy to the feed to produce a vapor from the feed;
   nucleating nanoscale powders from the vapor;
   thermally quenching said nucleated nanoscale powders;
   collecting the thermally quenched nanoscale powders,
      wherein the step of providing thermal energy raises a peak processing temperature to at least 3000 K; and
   wherein the process operates at a peak processing velocity greater than 46 feet per second.

2. The process of claim 1 wherein the thermal energy is provided in the form of plasma.

3. The process of claim 1 wherein the thermal energy is provided in the form of internal energy.

4. The process of claim 1 wherein the thermal energy is provided in the form of pulsed electric arc.

5. The process of claim 1 wherein the thermal energy is provided in the form of a combination of two or more methods selected from the group consisting of internal energy, heat of reaction, inductive, microwave, electromagnetic, direct electric arc, pulsed electric arc and nuclear.

6. The process of claim 1 wherein the nanoscale powders comprise an oxygen containing compound.

7. The process of claim 1 wherein the nanoscale powders comprise a metal containing compound.

8. The process of claim 1 wherein the nanoscale powers comprise a metal.

9. The process of claim 1 wherein the nanoscale powers comprise an alloy.

10. The process of claim 1 wherein the peak processing velocity is greater than 1 Mach.

11. A process for manufacturing nanoscale powders comprising:
providing a feed comprising fluid;
providing thermal energy to the feed to produce a vapor from the feed;
nucleating nanoscale powders from the vapor;
thermally quenching said nucleated nanoscale powders;
collecting the thermally quenched nanoscale powders, wherein the step of providing thermal energy raises a peak processing temperature to at least 3000 K; and
wherein the process operates at a peak processing velocity greater than 46 feet per second.

12. The process of claim 11 wherein the thermal energy is provided in the form of plasma.

13. The process of claim 11 wherein the thermal energy is provided in the form of internal energy.

14. The process of claim 11 wherein the thermal energy is provided in the form of pulsed electric arc.

15. The process of claim 11 wherein the thermal energy is provided in the form of a combination of two or more of methods selected from the group consisting of internal energy, heat of reaction, inductive, microwave, electromagnetic, direct electric arc, pulsed electric arc and nuclear.

16. The process of claim 11 wherein the nanoscale powders comprise an oxygen containing compound.

17. The process of claim 11 wherein the nanoscale powders comprise a metal containing compound.

18. The process of claim 11 wherein the nanoscale powers comprise a metal.

19. The process of claim 11 wherein the nanoscale powers comprise an alloy.

20. The process of claim 11 wherein the peak processing velocity is greater than 1 Mach.

21. The process of claim 1 wherein the nanoscale powders comprise a ceramic.

22. The process of claim 11 wherein the nanoscale powders comprise a ceramic.

23. The process of claim 1 wherein the nanoscale powders comprise an intermetallic.

24. The process of claim 11 wherein the nanoscale powders comprise an intermetallic.

25. A process for manufacturing nanoscale powders comprising:
providing a feed comprising a precursor in powder form suspended in a gas;
providing thermal energy to the feed thereby converting the precursor in powder form into a stream comprising vapor;
providing an extended reaction zone downstream of the step of providing thermal energy wherein the stream comprising vapor is condensed to nucleate solid nanoscale powders by adjusting the thermokinetic state of the stream comprising vapor;
providing a thermal quench of the solid nanoscale powders;
collecting the thermally quenched solid nanoscale powders;
wherein the step of providing thermal energy raises the peak processing temperature to at least 3000 K; and
wherein the process operates at a peak processing velocity greater than 46 feet per second.

26. The process of claim 25 wherein the thermal energy is provided in the form of plasma.

27. The process of claim 25 wherein the thermal energy is provided in the form of internal energy.

28. The process of claim 25 wherein the thermal energy is provided in the form of pulsed electric arc.

29. The process of claim 25 wherein the thermal energy is provided in the form of a combination of two or more of methods selected from the group consisting of internal energy, heat of reaction, inductive, microwave, electromagnetic, direct electric arc, pulsed electric arc and nuclear.

30. The process of claim 25 wherein the nanoscale powders comprise an oxygen containing compound.

31. The process of claim 25 wherein the nanoscale powders comprise a metal containing compound.

32. The process of claim 25 wherein the nanoscale powders comprise a metal.

33. The process of claim 25 wherein the nanoscale powders comprise an alloy.

34. The process of claim 25 wherein the precursor in powder form suspended in a gas has a particle size greater than 1 micrometer.

35. The process of claim 25 wherein the gas comprises oxygen.

36. A process for manufacturing nanoscale powders comprising:
providing a feed comprising a precursor in powder form suspended in a gas;
providing thermal energy to the feed thereby converting the precursor in powder form into a stream comprising vapor;
providing an extended reaction zone downstream of the step of providing thermal energy thereby providing additional residence time to the stream comprising vapor;
providing an additional zone downstream of the extended reaction zone wherein the stream comprising vapor is condensed to nucleate solid nanoscale powders by adjusting the thermokinetic state of the stream comprising vapor;
providing a thermal quench of the solid nanoscale powders downstream of the additional zone;
collecting the thermally quenched solid nanoscale powders; and
wherein the gas is selected to provide an oxidizing or reducing atmosphere during the step wherein the precursor in powder form is converted into a stream comprising vapor.

37. The process of claim 36 wherein the peak processing velocity is greater than 1 Mach.

38. The process of claim 36 wherein the nanoscale powders comprise an intermetallic.

39. The process of claim 36 wherein the nanoscale powders comprise a ceramic.

40. The process of claim 36 wherein the nanoscale powders comprise a composite.

41. The process of claim 36 wherein the thermokinetic state of the stream comprising vapor is adjusted by addition of an oxidizing, reducing or inert kinetic gas in the additional zone.

42. The process of claim 36 wherein the thermokinetic state of the stream comprising vapor is adjusted by reducing the temperature of the stream to achieve supersaturation, wherein the supersaturation causes condensation of solid nanoscale powders in the additional zone.

43. The process of claim 42 wherein the condensed solid nanoscale powders have an average grain size less than 100 nm.

44. The process of claim 42 wherein the condensed solid nanoscale powders have an average grain size less than 50 nm.

45. The process of claim 42 wherein the condensed solid nanoscale powders have an average grain size less than 30 nm.

46. The process of claim 42 wherein the condensed solid nanoscale powders have an average grain size less than 20 nm.

47. The process of claim 36 wherein the thermokinetic state of the stream comprising vapor is adjusted to achieve control of one or more of desired characteristics of nanoscale powders and wherein the desired characteristics is selected from the group: mean size of nanoscale powders, size distribution of nanoscale powders, phase of nanoscale powders, composition of nanoscale powders and interface of nanoscale powders.

48. The process of claim 36 wherein the gas used to suspend the precursor is selected to achieve control of one or more of desired characteristics of nanoscale powders and wherein the desired characteristics is selected from the group: mean size of nanoscale powders, size distribution of nanoscale powders, phase of nanoscale powders, composition of nanoscale powders and interface of nanoscale powders.

* * * * *